United States Patent
Fukunaga

(10) Patent No.: US 8,603,759 B2
(45) Date of Patent: Dec. 10, 2013

(54) RECOMBINANT PROTEIN CAPABLE OF BINDING SPECIFICALLY AND QUICKLY TO TROPONIN I DERIVED FROM HUMAN MYOCARDIUM

(71) Applicant: Panasonic Corporation, Osaka (JP)

(72) Inventor: Atsushi Fukunaga, Osaka (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 13/627,792

(22) Filed: Sep. 26, 2012

(65) Prior Publication Data

US 2013/0143245 A1   Jun. 6, 2013

Related U.S. Application Data

(63) Continuation of application No. PCT/JP2012/001505, filed on Mar. 5, 2012.

(30) Foreign Application Priority Data

Dec. 6, 2011  (JP) ................................ 2011-266579

(51) Int. Cl.
G01N 33/53  (2006.01)
C07K 16/00  (2006.01)
C12P 21/08  (2006.01)

(52) U.S. Cl.
USPC ....................... 435/7.1; 530/388.1; 530/387.3

(58) Field of Classification Search
None
See application file for complete search history.

(56) References Cited

U.S. PATENT DOCUMENTS

| | | | |
|---|---|---|---|
| 5,834,220 A * | 11/1998 | Wicks et al. | 435/7.92 |
| 6,991,907 B1 * | 1/2006 | Buechler et al. | 435/7.1 |
| 7,285,418 B2 * | 10/2007 | Katrukha et al. | 436/16 |
| 7,838,250 B1 * | 11/2010 | Goix et al. | 435/7.1 |
| 8,030,026 B2 | 10/2011 | Brophy et al. | |
| 2010/0216720 A1 | 8/2010 | Brophy et al. | |
| 2012/0076803 A1 | 3/2012 | Brophy et al. | |
| 2013/0158237 A1 * | 6/2013 | Fukunaga | 530/387.3 |

FOREIGN PATENT DOCUMENTS

WO  WO-2010/099079 A1  9/2010

OTHER PUBLICATIONS

Aleksei G. Katrukha et al., "Troponin I is released in bloodstream of patients with acute myocardial infarction not in free form but as complex", Clinical Chemistry, vol. 43, Issue 8, pp. 1379-1385 (1997).
Till Keller et al., "Sensitive Troponin I Assay in Early Diagnosis of Acute Myocardial Infarction," The New England Journal of Medicine, vol. 361, pp. 868-877 (2009).
Jun Kamishikiryo et al., "Molecular Basis for LLT1 Protein Recognition by Human CD161 Protein (NKRP1A/KLRB1)", The Journal of Biological Chemistry, vol. 286, No. 27, pp. 23823-23830.
G. Kohler et al., Nature, 256, 495(1975).
International Search Report mailed May 22, 2012 issued in corresponding International Application No. PCT/JP2012/001505.

* cited by examiner

*Primary Examiner* — Shulamith H Shafer
(74) *Attorney, Agent, or Firm* — McDermott Will & Emery LLP

(57) ABSTRACT

Provided is a recombination protein which binds specifically to troponin I derived from human myocardium. The recombinant protein includes a light chain variable region consisting of the amino acid sequence represented by SEQ ID NO: 63; and a heavy chain variable region consisting of the amino acid sequence represented by SEQ ID NO: 65.

12 Claims, 2 Drawing Sheets

SEQUENCE LISTING

```
<160> NUMBER OF SEQ ID NOS: 71

<210> SEQ ID NO 1
<211> LENGTH: 46
<212> TYPE: PRT
<213> ORGANISM: Homo sapiens

<400> SEQUENCE: 1

Arg Pro Ala Pro Ala Pro Ile Arg Arg Ser Ser Asn Tyr Arg Ala
1               5                   10                  15

Tyr Ala Thr Glu Pro His Ala Lys Lys Lys Ser Lys Ile Ser Ala Ser
                20                  25                  30

Arg Lys Leu Gln Leu Lys Thr Leu Leu Leu Gln Ile Ala Lys
            35                  40                  45

<210> SEQ ID NO 2
<211> LENGTH: 50
<212> TYPE: DNA
<213> ORGANISM: Artificial
<220> FEATURE:
<223> OTHER INFORMATION: primer

<400> SEQUENCE: 2
cctttctatg cggcccagcc ggccatggcc gayattgtwc tcwcccartc           50

<210> SEQ ID NO 3
<211> LENGTH: 50
```

```
<212> TYPE: DNA
<213> ORGANISM: Artificial
<220> FEATURE:
<223> OTHER INFORMATION: primer

<400> SEQUENCE: 3
cctttctatg cggcccagcc ggccatggcc gayattstgm tsacycagtc          50

<210> SEQ ID NO 4
<211> LENGTH: 50
<212> TYPE: DNA
<213> ORGANISM: Artificial
<220> FEATURE:
<223> OTHER INFORMATION: primer

<400> SEQUENCE: 4
cctttctatg cggcccagcc ggccatggcc gayattgtgm tmactcagtc          50

<210> SEQ ID NO 5
<211> LENGTH: 50
<212> TYPE: DNA
<213> ORGANISM: Artificial
<220> FEATURE:
<223> OTHER INFORMATION: primer

<400> SEQUENCE: 5
cctttctatg cggcccagcc ggccatggcc gayattgtgh trwcacagtc          50

<210> SEQ ID NO 6
<211> LENGTH: 50
<212> TYPE: DNA
<213> ORGANISM: Artificial
<220> FEATURE:
<223> OTHER INFORMATION: primer

<400> SEQUENCE: 6
cctttctatg cggcccagcc ggccatggcc gayattgtra tgacmcagtc          50

<210> SEQ ID NO 7
<211> LENGTH: 50
<212> TYPE: DNA
<213> ORGANISM: Artificial
<220> FEATURE:
<223> OTHER INFORMATION: primer

<400> SEQUENCE: 7
cctttctatg cggcccagcc ggccatggcc gayattmaga tramccagtc          50

<210> SEQ ID NO 8
<211> LENGTH: 50
<212> TYPE: DNA
<213> ORGANISM: Artificial
<220> FEATURE:
<223> OTHER INFORMATION: primer

<400> SEQUENCE: 8
cctttctatg cggcccagcc ggccatggcc gayattcaga tgaydcagtc          50

<210> SEQ ID NO 9
<211> LENGTH: 50
<212> TYPE: DNA
<213> ORGANISM: Artificial
<220> FEATURE:
<223> OTHER INFORMATION: primer

<400> SEQUENCE: 9
cctttctatg cggcccagcc ggccatggcc gayattttgc tgactcagtc          50
```

<210> SEQ ID NO 10
<211> LENGTH: 50
<212> TYPE: DNA
<213> ORGANISM: Artificial
<220> FEATURE:
<223> OTHER INFORMATION: primer

<400> SEQUENCE: 10
cctttctatg cggcccagcc ggccatggcc gayattgttc tcawccagtc          50

<210> SEQ ID NO 11
<211> LENGTH: 50
<212> TYPE: DNA
<213> ORGANISM: Artificial
<220> FEATURE:
<223> OTHER INFORMATION: primer

<400> SEQUENCE: 11
cctttctatg cggcccagcc ggccatggcc gayattgwgc tsacccaatc          50

<210> SEQ ID NO 12
<211> LENGTH: 50
<212> TYPE: DNA
<213> ORGANISM: Artificial
<220> FEATURE:
<223> OTHER INFORMATION: primer

<400> SEQUENCE: 12
cctttctatg cggcccagcc ggccatggcc gayattstra tgacccartc          50

<210> SEQ ID NO 13
<211> LENGTH: 50
<212> TYPE: DNA
<213> ORGANISM: Artificial
<220> FEATURE:
<223> OTHER INFORMATION: primer

<400> SEQUENCE: 13
cctttctatg cggcccagcc ggccatggcc gayrttktga tgacccavac          50

<210> SEQ ID NO 14
<211> LENGTH: 50
<212> TYPE: DNA
<213> ORGANISM: Artificial
<220> FEATURE:
<223> OTHER INFORMATION: primer

<400> SEQUENCE: 14
cctttctatg cggcccagcc ggccatggcc gayatycaga tgacacagac          50

<210> SEQ ID NO 15
<211> LENGTH: 50
<212> TYPE: DNA
<213> ORGANISM: Artificial
<220> FEATURE:
<223> OTHER INFORMATION: primer

<400> SEQUENCE: 15
cctttctatg cggcccagcc ggccatggcc gayattgtga tgacacaacc          50

<210> SEQ ID NO 16
<211> LENGTH: 50
<212> TYPE: DNA
<213> ORGANISM: Artificial
<220> FEATURE:
<223> OTHER INFORMATION: primer

```
<400> SEQUENCE: 16
cctttctatg cggcccagcc ggccatggcc gayatccagc tgactcagcc          50

<210> SEQ ID NO 17
<211> LENGTH: 50
<212> TYPE: DNA
<213> ORGANISM: Artificial
<220> FEATURE:
<223> OTHER INFORMATION: primer

<400> SEQUENCE: 17
cctttctatg cggcccagcc ggccatggcc gayattgtga tgacbcagkc          50

<210> SEQ ID NO 18
<211> LENGTH: 50
<212> TYPE: DNA
<213> ORGANISM: Artificial
<220> FEATURE:
<223> OTHER INFORMATION: primer

<400> SEQUENCE: 18
cctttctatg cggcccagcc ggccatggcc gayattgtga taacycagga          50

<210> SEQ ID NO 19
<211> LENGTH: 50
<212> TYPE: DNA
<213> ORGANISM: Artificial
<220> FEATURE:
<223> OTHER INFORMATION: primer

<400> SEQUENCE: 19
cctttctatg cggcccagcc ggccatggcc gayattgtga tgacccagwt          50

<210> SEQ ID NO 20
<211> LENGTH: 50
<212> TYPE: DNA
<213> ORGANISM: Artificial
<220> FEATURE:
<223> OTHER INFORMATION: primer

<400> SEQUENCE: 20
cctttctatg cggcccagcc ggccatggcc gaygtgstgm tsacycagtc          50

<210> SEQ ID NO 21
<211> LENGTH: 52
<212> TYPE: DNA
<213> ORGANISM: Artificial
<220> FEATURE:
<223> OTHER INFORMATION: primer

<400> SEQUENCE: 21
cctttctatg cggcccagcc ggccatggcc gaygctgttg tactcaggaa tc       52

<210> SEQ ID NO 22
<211> LENGTH: 50
<212> TYPE: DNA
<213> ORGANISM: Artificial
<220> FEATURE:
<223> OTHER INFORMATION: primer

<400> SEQUENCE: 22
cctttctatg cggcccagcc ggccatggcc gayattgtdh tvwchcagtc          50

<210> SEQ ID NO 23
<211> LENGTH: 53
```

<212> TYPE: DNA
<213> ORGANISM: Artificial
<220> FEATURE:
<223> OTHER INFORMATION: primer

<400> SEQUENCE: 23
agcggcggcg gcggctctgg tggtggtgga tccgakgtrm agcttcagga gyc    53

<210> SEQ ID NO 24
<211> LENGTH: 53
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (39)..(39)
<223> OTHER INFORMATION: n stands for any base

<400> SEQUENCE: 24
agcggcggcg gcggctctgg tggtggtgga tccgaggtnc agctbcagca gtc    53

<210> SEQ ID NO 25
<211> LENGTH: 53
<212> TYPE: DNA
<213> ORGANISM: Artificial
<220> FEATURE:
<223> OTHER INFORMATION: primer

<400> SEQUENCE: 25
agcggcggcg gcggctctgg tggtggtgga tcccaggtgc agctgaagsa stc    53

<210> SEQ ID NO 26
<211> LENGTH: 53
<212> TYPE: DNA
<213> ORGANISM: Artificial
<220> FEATURE:
<223> OTHER INFORMATION: primer

<400> SEQUENCE: 26
agcggcggcg gcggctctgg tggtggtgga tcccagstbc agctgcagca gtc    53

<210> SEQ ID NO 27
<211> LENGTH: 53
<212> TYPE: DNA
<213> ORGANISM: Artificial
<220> FEATURE:
<223> OTHER INFORMATION: primer

<400> SEQUENCE: 27
agcggcggcg gcggctctgg tggtggtgga tccgaggtyc agctycagca gtc    53

<210> SEQ ID NO 28
<211> LENGTH: 53
<212> TYPE: DNA
<213> ORGANISM: Artificial
<220> FEATURE:
<223> OTHER INFORMATION: primer

<400> SEQUENCE: 28
agcggcggcg gcggctctgg tggtggtgga tccgargtcc arctgcaaca rtc    53

<210> SEQ ID NO 29
<211> LENGTH: 53
<212> TYPE: DNA
<213> ORGANISM: Artificial
<220> FEATURE:
<223> OTHER INFORMATION: primer

<400> SEQUENCE: 29
agcggcggcg gcggctctgg tggtggtgga tcccaggtyc agctbcagca rtc        53

<210> SEQ ID NO 30
<211> LENGTH: 53
<212> TYPE: DNA
<213> ORGANISM: Artificial
<220> FEATURE:
<223> OTHER INFORMATION: primer

<400> SEQUENCE: 30
agcggcggcg gcggctctgg tggtggtgga tcccaggtyc arctkcagca gtc        53

<210> SEQ ID NO 31
<211> LENGTH: 53
<212> TYPE: DNA
<213> ORGANISM: Artificial
<220> FEATURE:
<223> OTHER INFORMATION: primer

<400> SEQUENCE: 31
agcggcggcg gcggctctgg tggtggtgga tcccaggtcc acgtgaagca gtc        53

<210> SEQ ID NO 32
<211> LENGTH: 53
<212> TYPE: DNA
<213> ORGANISM: Artificial
<220> FEATURE:
<223> OTHER INFORMATION: primer

<400> SEQUENCE: 32
agcggcggcg gcggctctgg tggtggtgga tccgaggtga asstggtgga rtc        53

<210> SEQ ID NO 33
<211> LENGTH: 53
<212> TYPE: DNA
<213> ORGANISM: Artificial
<220> FEATURE:
<223> OTHER INFORMATION: primer

<400> SEQUENCE: 33
agcggcggcg gcggctctgg tggtggtgga tccgavgtga wgytggtgga gtc        53

<210> SEQ ID NO 34
<211> LENGTH: 53
<212> TYPE: DNA
<213> ORGANISM: Artificial
<220> FEATURE:
<223> OTHER INFORMATION: primer

<400> SEQUENCE: 34
agcggcggcg gcggctctgg tggtggtgga tccgaggtga aggtcatcga gtc        53

<210> SEQ ID NO 35
<211> LENGTH: 53
<212> TYPE: DNA
<213> ORGANISM: Artificial
<220> FEATURE:
<223> OTHER INFORMATION: primer

<400> SEQUENCE: 35
agcggcggcg gcggctctgg tggtggtgga tccsaggtgc agskggtgga gtc        53

<210> SEQ ID NO 36
<211> LENGTH: 53

<212> TYPE: DNA
<213> ORGANISM: Artificial
<220> FEATURE:
<223> OTHER INFORMATION: primer

<400> SEQUENCE: 36
agcggcggcg gcggctctgg tggtggtgga tccgakgtgc amctggtgga gtc    53

<210> SEQ ID NO 37
<211> LENGTH: 53
<212> TYPE: DNA
<213> ORGANISM: Artificial
<220> FEATURE:
<223> OTHER INFORMATION: primer

<400> SEQUENCE: 37
agcggcggcg gcggctctgg tggtggtgga tccgaagtgc avctggtgga gtc    53

<210> SEQ ID NO 38
<211> LENGTH: 53
<212> TYPE: DNA
<213> ORGANISM: Artificial
<220> FEATURE:
<223> OTHER INFORMATION: primer

<400> SEQUENCE: 38
agcggcggcg gcggctctgg tggtggtgga tccgaggtga agctgatgga rtc    53

<210> SEQ ID NO 39
<211> LENGTH: 53
<212> TYPE: DNA
<213> ORGANISM: Artificial
<220> FEATURE:
<223> OTHER INFORMATION: primer

<400> SEQUENCE: 39
agcggcggcg gcggctctgg tggtggtgga tccgaggtgc arcttgttga gtc    53

<210> SEQ ID NO 40
<211> LENGTH: 53
<212> TYPE: DNA
<213> ORGANISM: Artificial
<220> FEATURE:
<223> OTHER INFORMATION: primer

<400> SEQUENCE: 40
agcggcggcg gcggctctgg tggtggtgga tccgargtra agcttctcga gtc    53

<210> SEQ ID NO 41
<211> LENGTH: 53
<212> TYPE: DNA
<213> ORGANISM: Artificial
<220> FEATURE:
<223> OTHER INFORMATION: primer

<400> SEQUENCE: 41
agcggcggcg gcggctctgg tggtggtgga tccgaagtga arsttgagga gtc    53

<210> SEQ ID NO 42
<211> LENGTH: 53
<212> TYPE: DNA
<213> ORGANISM: Artificial
<220> FEATURE:
<223> OTHER INFORMATION: primer

<400> SEQUENCE: 42
agcggcggcg gcggctctgg tggtggtgga tccgaagtga tgctggtgga gtc    53

<210> SEQ ID NO 43
<211> LENGTH: 55
<212> TYPE: DNA
<213> ORGANISM: Artificial
<220> FEATURE:
<223> OTHER INFORMATION: primer

<400> SEQUENCE: 43
agcggcggcg gcggctctgg tggtggtgga tcccaggtta ctctraaagw gtstg      55

<210> SEQ ID NO 44
<211> LENGTH: 53
<212> TYPE: DNA
<213> ORGANISM: Artificial
<220> FEATURE:
<223> OTHER INFORMATION: primer

<400> SEQUENCE: 44
agcggcggcg gcggctctgg tggtggtgga tcccaggtcc aaytvcagca rcc         53

<210> SEQ ID NO 45
<211> LENGTH: 53
<212> TYPE: DNA
<213> ORGANISM: Artificial
<220> FEATURE:
<223> OTHER INFORMATION: primer

<400> SEQUENCE: 45
agcggcggcg gcggctctgg tggtggtgga tccgatgtga acttggaagt gtc         53

<210> SEQ ID NO 46
<211> LENGTH: 53
<212> TYPE: DNA
<213> ORGANISM: Artificial
<220> FEATURE:
<223> OTHER INFORMATION: primer

<400> SEQUENCE: 46
accagagccg ccgccgccgc taccaccacc accccgtttg atttccarct tkg          53

<210> SEQ ID NO 47
<211> LENGTH: 53
<212> TYPE: DNA
<213> ORGANISM: Artificial
<220> FEATURE:
<223> OTHER INFORMATION: primer

<400> SEQUENCE: 47
accagagccg ccgccgccgc taccaccacc accccgtttt atttccagct tgg          53

<210> SEQ ID NO 48
<211> LENGTH: 53
<212> TYPE: DNA
<213> ORGANISM: Artificial
<220> FEATURE:
<223> OTHER INFORMATION: primer

<400> SEQUENCE: 48
accagagccg ccgccgccgc taccaccacc accccgttts agctccagct tgg          53

<210> SEQ ID NO 49
<211> LENGTH: 53
<212> TYPE: DNA
<213> ORGANISM: Artificial
<220> FEATURE:
<223> OTHER INFORMATION: primer

<400> SEQUENCE: 49
accagagccg ccgccgccgc taccaccacc accccgttyw atttccaact twg        53

<210> SEQ ID NO 50
<211> LENGTH: 53
<212> TYPE: DNA
<213> ORGANISM: Artificial
<220> FEATURE:
<223> OTHER INFORMATION: primer

<400> SEQUENCE: 50
accagagccg ccgccgccgc taccaccacc acccccctagg acagtcagtt tgg        53

<210> SEQ ID NO 51
<211> LENGTH: 45
<212> TYPE: DNA
<213> ORGANISM: Artificial
<220> FEATURE:
<223> OTHER INFORMATION: primer

<400> SEQUENCE: 51
cggcaccggc gcacctgcgg ccgcygagga aacggtgacc gtggt                  45

<210> SEQ ID NO 52
<211> LENGTH: 45
<212> TYPE: DNA
<213> ORGANISM: Artificial
<220> FEATURE:
<223> OTHER INFORMATION: primer

<400> SEQUENCE: 52
cggcaccggc gcacctgcgg ccgcygagga gactgtgaga gtggt                  45

<210> SEQ ID NO 53
<211> LENGTH: 45
<212> TYPE: DNA
<213> ORGANISM: Artificial
<220> FEATURE:
<223> OTHER INFORMATION: primer

<400> SEQUENCE: 53
cggcaccggr gcacctgcgg ccgcygagga gacggtgact gagrt                  45

<210> SEQ ID NO 54
<211> LENGTH: 45
<212> TYPE: DNA
<213> ORGANISM: Artificial
<220> FEATURE:
<223> OTHER INFORMATION: primer

<400> SEQUENCE: 54
cggcaccggc gcacctgcgg ccgcygagga agactgtaga gtggt                  45

<210> SEQ ID NO 55
<211> LENGTH: 45
<212> TYPE: DNA
<213> ORGANISM: Artificial
<220> FEATURE:
<223> OTHER INFORMATION: primer

<400> SEQUENCE: 55
cggcaccggc gcacctgcgg ccgcygcgga gacastgacc agagt                  45

<210> SEQ ID NO 56
<211> LENGTH: 45

<210> SEQ ID NO 57
<211> LENGTH: 345
<212> TYPE: DNA
<213> ORGANISM: Mus musculus

<400> SEQUENCE: 57

```
cagctgcagc tgcagcagtc tggggcagag cttgtgaggt caggggcctc agtcaagttg      60
tcctgcacag cttctggctt caacattaaa gactactata tgaactgggt gaagcagagg     120
cctgaacagg gcctgagtg gattggatgg attgatcctg cgaatggtga tactgcatat     180
gccccgaggt tccaggtcaa ggccactatg actgcagaca atcctccaa cacagcctac     240
ctgcagctca gcagcctgac atctgaggac actgccgtct attactgtaa tgctgatctc     300
cctatggacc agtggggtca aggaacctca gtcaccgtct cctca                    345
```

<210> SEQ ID NO 58
<211> LENGTH: 339
<212> TYPE: DNA
<213> ORGANISM: Mus musculus

<400> SEQUENCE: 58

```
gacgtggtgc tcactcagtc tccactcact ttgtcggtta ccattggaca accagcctcc      60
atctcttgca gtcaagtca gagcctctta gatagtgatg gaaagacata tttgaattgg     120
ttgttacaga ggccaggcca gtctccaaag cgcctaatct atctggtgtc taaactggac     180
tctggagtcc ctgacaggtt cactggcagt ggatcaggga cagatttcac actgaaaatc     240
agcagagtgg aggctgagga tttgggagtt tattattgct ggcaaggtac acatttttcct     300
ctcacgttcg gtgctgggac aaagttggaa attaaacgg                           339
```

<210> SEQ ID NO 59
<211> LENGTH: 729
<212> TYPE: DNA
<213> ORGANISM: Artificial
<220> FEATURE:
<223> OTHER INFORMATION: scFv gene coding for scFv antibody fragment

<400> SEQUENCE: 59

```
gacgtggtgc tcactcagtc tccactcact ttgtcggtta ccattggaca accagcctcc      60
atctcttgca gtcaagtca gagcctctta gatagtgatg gaaagacata tttgaattgg     120
ttgttacaga ggccaggcca gtctccaaag cgcctaatct atctggtgtc taaactggac     180
tctggagtcc ctgacaggtt cactggcagt ggatcaggga cagatttcac actgaaaatc     240
agcagagtgg aggctgagga tttgggagtt tattattgct ggcaaggtac acatttttcct     300
ctcacgttcg gtgctgggac aaagttggaa attaaacggg tggtggtgg atctggcggc     360
ggcggctctg gtggtggtgg atcccagctg cagctgcagc agtctggggc agagcttgtg     420
aggtcagggg cctcagtcaa gttgtcctgc acagcttctg gcttcaacat taaagactac     480
tatatgaact gggtgaagca gaggcctgaa cagggcctgg agtggattgg atggattgat     540
cctgcgaatg gtgatactgc atatgccccg aggttccagg tcaaggccac tatgactgca     600
gacaaatcct ccaacacagc ctacctgcag ctcagcagcc tgacatctga ggacactgcc     660
```

```
gtctattact gtaatgctga tctccctatg gaccagtggg gtcaaggaac ctcagtcacc    720
gtctcctcc                                                           729
```

<210> SEQ ID NO 60
<211> LENGTH: 63
<212> TYPE: DNA
<213> ORGANISM: Artificial
<220> FEATURE:
<223> OTHER INFORMATION: signal sequence of protein expressing vector
      pET22b(+)

<400> SEQUENCE: 60

```
aaatacctgc tgccgaccgc tgctgctggt ctgctgctcc tcgctgccca gccggcgatg    60
gcc                                                                 63
```

<210> SEQ ID NO 61
<211> LENGTH: 254
<212> TYPE: PRT
<213> ORGANISM: Artificial
<220> FEATURE:
<223> OTHER INFORMATION: mutant scFv antibody fragment

<400> SEQUENCE: 61

```
Asp Val Val Leu Thr Gln Ser Pro Leu Thr Leu Ser Val Thr Ile Gly
1               5                   10                  15

Gln Pro Ala Ser Ile Ser Cys Lys Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Asp Gly Val Pro
    50                  55                  60

Asp Arg Phe Asp Gly Asp Gly Asp Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Leu Thr Phe Gly Ala Gly Thr Lys Leu Glu Ile Lys
            100                 105                 110

Arg Gly Gly Gly Gly Ser Gly Gly Gly Gly Ser Gly Gly Gly Gly Ser
        115                 120                 125

Gln Leu Gln Leu Gln Gln Ser Gly Ala Glu Leu Val Arg Ser Gly Ala
    130                 135                 140

Ser Val Lys Leu Ser Cys Thr Ala Ser Gly Phe Asn Ile Lys Asp Tyr
145                 150                 155                 160

Tyr Met Asn Trp Val Lys Gln Arg Pro Glu Gln Gly Leu Glu Trp Ile
                165                 170                 175

Gly Trp Ile Asp Pro Ala Asn Gly Asp Thr Ala Tyr Ala Pro Arg Phe
            180                 185                 190

Gln Val Lys Ala Thr Met Thr Ala Asp Lys Ser Ser Asn Thr Ala Tyr
        195                 200                 205

Leu Gln Leu Ser Ser Leu Thr Ser Glu Asp Thr Ala Val Tyr Tyr Cys
    210                 215                 220

Asn Ala Asp Leu Pro Met Asp Gln Trp Gly Gln Gly Thr Ser Val Thr
225                 230                 235                 240

Val Ser Ser Ala Ala Ala Leu Glu His His His His His His
                245                 250
```

<210> SEQ ID NO 62

<211> LENGTH: 254
<212> TYPE: PRT
<213> ORGANISM: Artificial
<220> FEATURE:
<223> OTHER INFORMATION: wild-type scFv antibody fragment

<400> SEQUENCE: 62

```
Asp Val Val Leu Thr Gln Ser Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Leu Thr Phe Gly Ala Gly Thr Lys Leu Glu Ile Lys
            100                 105                 110

Arg Gly Gly Gly Gly Ser Gly Gly Gly Ser Gly Gly Gly Gly Ser
        115                 120                 125

Gln Leu Gln Leu Gln Gln Ser Gly Ala Glu Leu Val Arg Ser Gly Ala
    130                 135                 140

Ser Val Lys Leu Ser Cys Thr Ala Ser Gly Phe Asn Ile Lys Asp Tyr
145                 150                 155                 160

Tyr Met Asn Trp Val Lys Gln Arg Pro Glu Gln Gly Leu Glu Trp Ile
                165                 170                 175

Gly Trp Ile Asp Pro Ala Asn Gly Asp Thr Ala Tyr Ala Pro Arg Phe
            180                 185                 190

Gln Val Lys Ala Thr Met Thr Ala Asp Lys Ser Ser Asn Thr Ala Tyr
        195                 200                 205

Leu Gln Leu Ser Ser Leu Thr Ser Glu Asp Thr Ala Val Tyr Tyr Cys
    210                 215                 220

Asn Ala Asp Leu Pro Met Asp Gln Trp Gly Gln Gly Thr Ser Val Thr
225                 230                 235                 240

Val Ser Ser Ala Ala Ala Leu Glu His His His His His
                245                 250
```

<210> SEQ ID NO 63
<211> LENGTH: 113
<212> TYPE: PRT
<213> ORGANISM: Artificial
<220> FEATURE:
<223> OTHER INFORMATION: VL of mutant scFv antibody fragment

<400> SEQUENCE: 63

```
Asp Val Val Leu Thr Gln Ser Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Asp Gly Val Pro
    50                  55                  60

Asp Arg Phe Asp Gly Asp Gly Asp Gly Thr Asp Phe Thr Leu Lys Ile
65                  70                  75                  80
```

```
Ser Arg Val Glu Ala Glu Asp Leu Gly Val Tyr Tyr Cys Trp Gln Gly
                85                  90                  95

Thr His Phe Pro Leu Thr Phe Gly Ala Gly Thr Lys Leu Glu Ile Lys
            100                 105                 110

Arg

<210> SEQ ID NO 64
<211> LENGTH: 15
<212> TYPE: PRT
<213> ORGANISM: Artificial
<220> FEATURE:
<223> OTHER INFORMATION: linker for binding VH to VL

<400> SEQUENCE: 64

Gly Gly Gly Gly Ser Gly Gly Gly Gly Ser Gly Gly Gly Gly Ser
1               5                   10                  15

<210> SEQ ID NO 65
<211> LENGTH: 115
<212> TYPE: PRT
<213> ORGANISM: Artificial
<220> FEATURE:
<223> OTHER INFORMATION: VH of scFv antibody fragment

<400> SEQUENCE: 65

Gln Leu Gln Leu Gln Gln Ser Gly Ala Glu Leu Val Arg Ser Gly Ala
1               5                   10                  15

Ser Val Lys Leu Ser Cys Thr Ala Ser Gly Phe Asn Ile Lys Asp Tyr
            20                  25                  30

Tyr Met Asn Trp Val Lys Gln Arg Pro Glu Gln Gly Leu Glu Trp Ile
        35                  40                  45

Gly Trp Ile Asp Pro Ala Asn Gly Asp Thr Ala Tyr Ala Pro Arg Phe
    50                  55                  60

Gln Val Lys Ala Thr Met Thr Ala Asp Lys Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Ala Asp Leu Pro Met Asp Gln Trp Gly Gln Gly Thr Ser Val Thr
            100                 105                 110

Val Ser Ser
        115

<210> SEQ ID NO 66
<211> LENGTH: 11
<212> TYPE: PRT
<213> ORGANISM: Artificial
<220> FEATURE:
<223> OTHER INFORMATION: amino acid which modifies the c-terminal of the
      mutant scFv antibody fragment

<400> SEQUENCE: 66

Ala Ala Ala Leu Glu His His His His His His
1               5                   10

<210> SEQ ID NO 67
<211> LENGTH: 26
<212> TYPE: DNA
<213> ORGANISM: Artificial
<220> FEATURE:
<223> OTHER INFORMATION: primer

<400> SEQUENCE: 67
```

-continued gatattgtaa tgacccagtc tccatc  26

<210> SEQ ID NO 68
<211> LENGTH: 45
<212> TYPE: DNA
<213> ORGANISM: Artificial
<220> FEATURE:
<223> OTHER INFORMATION: primer

<400> SEQUENCE: 68
catatgtaaa tctccttatt aaagttaaac aaaattattc tagag  45

<210> SEQ ID NO 69
<211> LENGTH: 76
<212> TYPE: DNA
<213> ORGANISM: Artificial
<220> FEATURE:
<223> OTHER INFORMATION: primer

<400> SEQUENCE: 69
ctatctggtg tctaaactgg acgatggagt ccctgacagg ttcgatggcg atggagatgg  60
gacagatttc acactg  76

<210> SEQ ID NO 70
<211> LENGTH: 76
<212> TYPE: DNA
<213> ORGANISM: Artificial
<220> FEATURE:
<223> OTHER INFORMATION: primer

<400> SEQUENCE: 70
cagtgtgaaa tctgtcccat ctccatcgcc atcgaacctg tcaggactc catcgtccag  60 tttagacacc agatag  76

<210> SEQ ID NO 71
<211> LENGTH: 762
<212> TYPE: DNA
<213> ORGANISM: Artificial
<220> FEATURE:
<223> OTHER INFORMATION: DNA sequence coding for mutant scFv antibody
      fragment

<400> SEQUENCE: 71
gacgtggtgc tcactcagtc tccactcact ttgtcggtta ccattggaca accagcctcc  60
atctcttgca gtcaagtca gagcctctta gatagtgatg aaagacata tttgaattgg  120 ttgttacaga ggccaggcca gtctccaaag cgcctaatct atctggtgtc taaactggac  180
gatggagtcc ctgacaggtt cgatggcgat ggagatggga cagatttcac actgaaaatc  240
agcagagtgg aggctgagga tttgggagtt tattattgct ggcaaggtac acattttcct  300
ctcacgttcg gtgctgggac aaagttggaa attaaacggg tggtggtgg atctggcggc  360 ggcggctctg gtggtggtgg atcccagctg cagctgcagc agtctgggc agagcttgtg  420 aggtcagggg cctcagtcaa gttgtcctgc acagcttctg gcttcaacat taaagactac  480
tatatgaact gggtgaagca gaggcctgaa cagggcctgg agtggattgg atggattgat  540
cctgcgaatg gtgatactgc atatgccccg aggttccagg tcaaggccac tatgactgca  600
gacaaatcct ccaacacagc ctacctgcag ctcagcagcc tgacatctga ggacactgcc  660
gtctattact gtaatgctga tctccctatg gaccagtggg gtcaaggaac ctcagtcacc  720
gtctcctcag cggccgcact cgagcaccac caccaccacc ac  762

RECOMBINANT PROTEIN CAPABLE OF BINDING SPECIFICALLY AND QUICKLY TO TROPONIN I DERIVED FROM HUMAN MYOCARDIUM

CROSS-REFERENCE TO RELATED APPLICATIONS

This is a continuation application of International Application No. PCT/JP2012/001505, with an international filing date of Mar. 5, 2012, which claims priority of Japanese Patent Application No. 2011-266579, filed on Dec. 6, 2011, the entire contents of each of which are incorporated herein by reference.

The Sequence listing in "SEQUENCE LISTING.TXT" created on Dec. 17, 2012 and being 21.0 KB in size is incorporated by reference and is identical to the sequence information in the instant application.

BACKGROUND OF THE INVENTION

1. Technical Field

The technical field relates to a recombinant protein capable of binding specifically and quickly to troponin I derived from human myocardium.

2. Description of Related Art

Non Patent Literature 1 and Non Patent Literature 2 disclose that a concentration of troponin I derived from myocardial increases rapidly in the blood of a patient who has suffered acute myocardial infarction.

CITATION LIST

Non Patent Literature

Non Patent Literature 1
Aleksei G. Katrukha et. al., "Troponin I is released in bloodstream of patients with acute myocardial infarction not in free form but as complex", Clinical Chemistry, Vol. 43, Issue 8, p.p. 1379-1385 (1997)

Non Patent Literature 2
Till Keller et. al., "Sensitive Troponin I Assay in Early Diagnosis of Acute Myocardinal Infarction", The NEW ENGLAND JOURNAL of MEDICINE, Vol. 361, pages 868-877 (2009)

SUMMARY

One non-limiting and exemplary embodiment provides a recombinant protein capable of binding specifically and quickly to troponin I derived from human myocardium.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

In one general aspect, the techniques disclosed here feature a recombinant protein which binds specifically to troponin I derived from human myocardium. The recombinant protein includes a light chain variable region consisting of the amino acid sequence represented by SEQ ID NO: 63, and a heavy chain variable region consisting of the amino acid sequence represented by SEQ ID NO: 65.

The present disclosure provides a recombinant protein capable of binding specifically and quickly to troponin I derived from human myocardium.

The recombinant protein and the method of the present disclosure can be used for early detection of acute myocardial infarction.

DETAILED DESCRIPTION

The embodiment of the present disclosure is described below.

(Explanation of Terms)

First, the terms used in the present specification are described.

Figure 1:
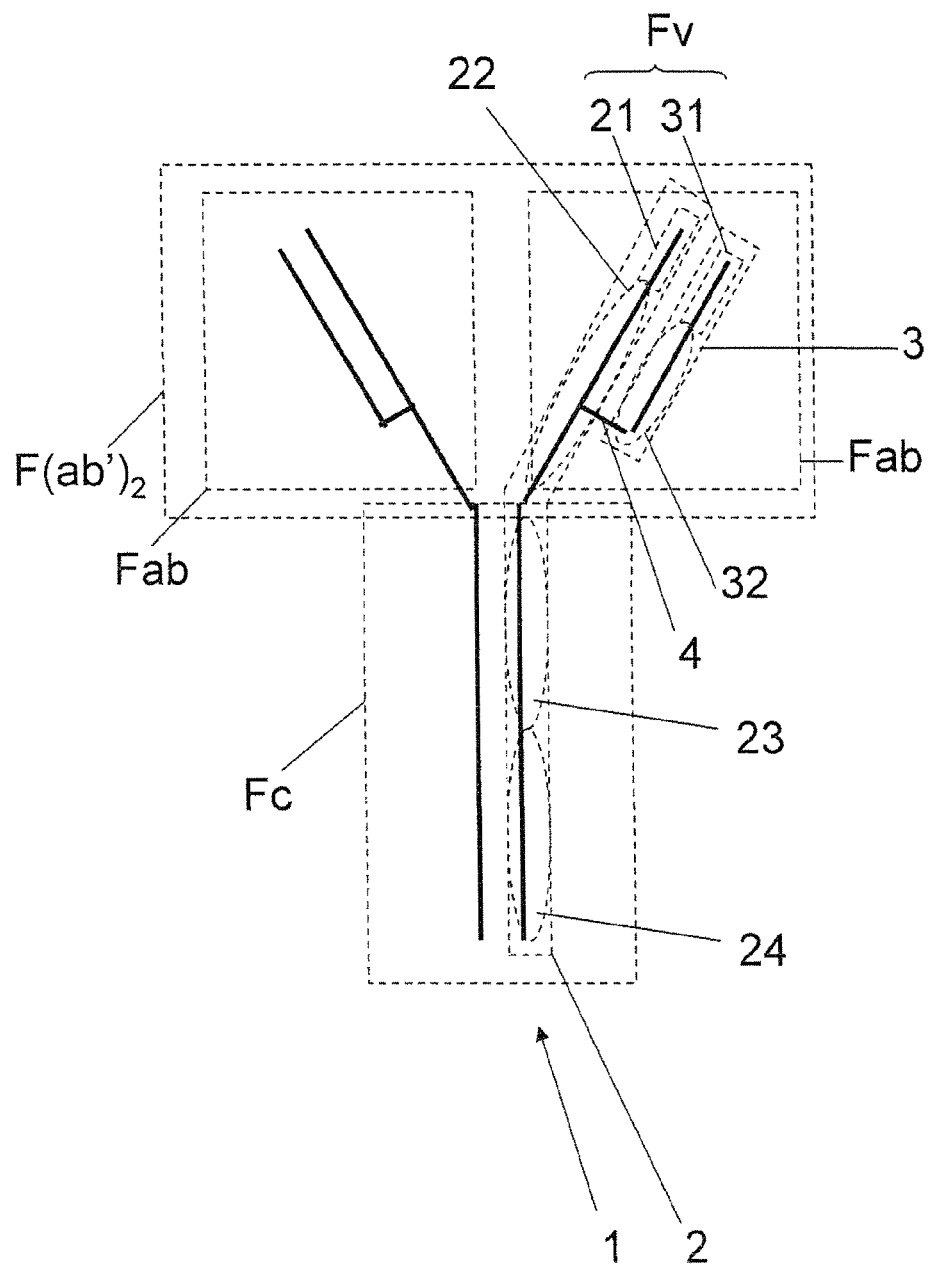
FIG. 1 shows an antibody.

FIG. 1 shows an antibody. The antibody 1 has a letter "Y" shape. The antibody 1 has two Fab regions and one Fc region. The antibody 1 consists of two heavy chains 2 and two light chains 3. Each heavy chain 2 consists of a heavy chain constant region 1 (22), a heavy chain constant region 2 (23), a heavy chain constant region 3 (24) and a heavy chain variable region 21. Each light chain 3 consists of a light chain variable region 31 and a light chain constant region 32.

Each Fab region consists of the one heavy chain variable region 21, the one heavy chain constant region 1 (22), the one light chain variable region 31, and the one light chain constant region 32. The light chain 3 is connected to the heavy chain 2 through a linker 4. The one heavy variable region 21 is present at the end of the heavy chain 2. The one light chain variable region 31 is present at the end of the light chain 3. An antigen is specifically bound to the antibody 1. In more detail, the antigen is bound specifically to the Fv region, which consists of the heavy chain variable region 21 and the light chain variable region 31. In the present specification, the antigen is troponin I derived from human myocardium.

The recombination protein according to the embodiment includes the light chain variable region 31 consisting of the amino acid sequence represented by SEQ ID NO: 63 and the heavy chain variable region 21 consists of the amino acid sequence represented by SEQ ID NO: 65. The recombinant protein of the present disclosure binds specifically and quickly to the troponin I derived from human myocardium.

The recombinant protein of the present disclosure may be either an antibody or an antibody fragment.

The antibody has a shape of the form of the letter "Y" shown in FIG. 1. The light chain variable region 31 and the heavy chain variable region 21, both of which is included in the antibody of the present disclosure, consist of amino acid sequences represented by SEQ ID NO: 63 and SEQ ID NO: 65, respectively. In the antibody, the light chain variable region 31 is connected to the heavy chain variable region 21 through a linker (not shown).

Examples of the antibody fragment include a Fab antibody fragment, a F(ab')$_2$ antibody fragment and an scFv antibody fragment.

The Fab antibody fragment consists of one Fab region. In other words, the Fab antibody fragment consists of the one light chain variable region 31 (SEQ ID NO: 63), the one heavy chain variable region 21 (SEQ ID NO: 65), the one light chain constant region 32, the one heavy chain constant region 1 (22), and the linker 4. The light chain constant region 32 is connected to the heavy chain constant region 1 (22) through the linker 4.

The F(ab')$_2$ antibody fragment consists of two Fab regions. As above, each Fab region consists of the one light chain variable region 31 (SEQ ID NO: 63), the one heavy chain variable region 21 (SEQ ID NO: 65), the one light chain constant region 32, the one heavy chain constant region 1 (22), and the linker 4. These two Fab regions are connected to each other through another linker (not shown). For example, one heavy chain constant region 1 (22) is connected to the other heavy chain constant region 1 (22) through another linker (not shown).

The scFv antibody fragment consists of the light chain variable region 31 (SEQ ID NO: 63), the heavy chain variable region 21 (SEQ ID NO: 65), and a linker. The light chain variable region 31 (SEQ ID NO: 63) is connected to the heavy chain variable region 21 (SEQ ID NO: 65) through a linker (not shown).

As long as the recombination protein is capable of binding specifically and quickly to troponin I derived from human myocardium, the linker connecting the light chain variable region 31 (SEQ ID NO: 63) and the heavy chain variable region 21 (SEQ ID NO: 65) is not specifically limited. An example of the linker is a peptide consisting of 5-20 amino acids. For example, the linker is a peptide consisting of the amino acid sequence represented by GGGGSGGGGSGGGGS (SEQ ID NO: 64). Another example of the linker is a disulfide bond (-sulfur atom (S)-sulfur atom (S)—).

As long as the recombination protein is capable of binding specifically and quickly to troponin I derived from human myocardium, the N-terminal of the light chain variable region 31 (SEQ ID NO: 63) may be modified with an amino acid sequence. The C-terminal thereof may be also modified.

As long as the recombination protein is capable of binding specifically and quickly to troponin I derived from human myocardium, the N-ten final of the heavy chain variable region 21 (SEQ ID NO: 65) may be modified with an amino acid sequence. The C-terminal thereof may be also modified. An example of the amino acid sequence to modify the C-terminal of the heavy chain variable region 21 (SEQ ID NO: 65) is AAALEHHHHHH (SEQ ID NO: 66).

When the recombinant protein of the present disclosure is brought into contact with troponin I derived from human myocardium, the recombinant protein of the present disclosure binds specifically and quickly to the troponin I derived from human myocardium. For example, when the recombinant protein of the present disclosure is mixed with troponin I derived from human myocardium, the recombinant protein of the present disclosure binds specifically and quickly to the troponin I derived from human myocardium.

Detection of the binding of the recombinant protein of the present disclosure to the troponin I derived from human myocardium can be carried out by methods for detecting antigen-antibody binding which are well known to those skilled in the art. Examples of such methods include the ELISA sandwich method.

The recombinant protein of the present disclosure can be produced using an ordinal protein expression technique. For example, first, a vector including a gene sequence coding for the recombinant protein of the present disclosure is prepared. An example of the vector is a plasmid. Then, cells (e.g., *Escherichia coli*) are transformed with this vector. These cells are incubated to produce the recombinant protein of the present disclosure.

In order to obtain the scFv antibody fragment efficiently, it is beneficial that the recombinant protein of the present disclosure is produced by a refolding method. Non Patent Literature 3 discloses the refolding method.

Non Patent Literature 3

Jun Kamishikiryo et. al., "Molecular Basis for LLT1 Protein Recognition by Human CD161 Protein (NKRP1A/KLRB1)", THE JOURNAL OF BIOLOGICAL CHEMISTRY, VOL. 286, NO. 27, p.p. 23823-23830.

Examples of the technique of the present disclosure are as follows.

1st aspect: A recombinant protein which binds specifically to troponin I derived from human myocardium. The recombinant protein includes a light chain variable region consisting of the amino acid sequence represented by SEQ ID NO: 63, and a heavy chain variable region consisting of the amino acid sequence represented by SEQ ID NO: 65.

2nd aspect: In the recombinant protein according to the 1st aspect, the recombinant protein may be an antibody.

3rd aspect: In the recombinant protein according to the 1st aspect, the recombinant protein may be an antibody fragment.

4th aspect: In the recombinant protein according to the 3rd aspect, the antibody fragment may be a Fab antibody fragment.

5th aspect: In the recombinant protein according to the 3rd aspect, the antibody fragment may be a F(ab')$_2$ antibody fragment.

6th aspect: In the recombinant protein according to the 3rd aspect, the antibody fragment may be an scFv antibody fragment.

7th aspect: A method for binding a recombinant protein specifically to troponin I derived from human myocardium, includes the following steps. A step (a) is a step of preparing the recombinant protein. T the recombinant protein includes a light chain variable region consisting of the amino acid sequence represented by SEQ ID NO: 63, and a heavy chain variable region consisting of the amino acid sequence represented by SEQ ID NO: 65. A step (b) is a step of bringing the recombinant protein into contact with the troponin I derived from human myocardium to bind the recombinant protein specifically to the troponin I derived from human myocardium. In this aspect, for example, the step (b) may be carried out in vitro.

8th aspect: In the method according to the 7th aspect, the recombinant protein may be an antibody.

9th aspect: In the method according to the 7th aspect, the recombinant protein may be an antibody fragment.

10th aspect: In the method according to the 9th aspect, the antibody fragment may be a Fab antibody fragment.

11th aspect: In the method according to the 9th aspect, the antibody fragment may be a F(ab')$_2$ antibody fragment.

12th aspect: In the method according to the 9th aspect, the antibody fragment may be scFv antibody fragment.

EXAMPLES

An example for supporting an exemplary embodiment of the present disclosure is described below.

Example 1

Table 1, Table 2, Table 3, and Table 4 show the primers used in Example 1,

Table 1 shows the forward mixture primers (primers 1-21, SEQ ID NOS: 02-22) for amplifying a light chain variable region.

Table 2 shows the forward mixture primers (primers 22-44, SEQ ID NOS: 23-45) for amplifying a heavy chain variable region.

Table 3 shows the reverse mixture primers (primers 45-49, SEQ ID NOS: 46-50) for amplifying a light chain variable region.

Table 4 shows the reverse mixture primers (primers 50-55, SEQ ID NOS: 51-56) for amplifying a heavy chain variable region.

TABLE 1

| Primer 1 | SEQ ID NO: 02 | CCTTTCTATGCGGCCCAGCCGGCCATG GCCGAYATTGTWCTCWCCCARTC |
|---|---|---|
| Primer 2 | SEQ ID NO: 03 | CCTTTCTATGCGGCCCAGCCGGCCATG GCCGAYATTSTGMTSACYCAGTC |
| Primer 3 | SEQ ID NO: 04 | CCTTTCTATGCGGCCCAGCCGGCCATG GCCGAYATTGTGMTMACTCAGTC |
| Primer 4 | SEQ ID NO: 05 | CCTTTCTATGCGGCCCAGCCGGCCATG GCCGAYATTGTGHTRWCACAGTC |
| Primer 5 | SEQ ID NO: 06 | CCTTTCTATGCGGCCCAGCCGGCCATG GCCGAYATTGTRATGACMCAGTC |
| Primer 6 | SEQ ID NO: 07 | CCTTTCTATGCGGCCCAGCCGGCCATG GCCGAYATTMAGATRAMCCAGTC |
| Primer 7 | SEQ ID NO: 08 | CCTTTCTATGCGGCCCAGCCGGCCATG GCCGAYATTCAGATGAYDCAGTC |
| Primer 8 | SEQ ID NO: 09 | CCTTTCTATGCGGCCCAGCCGGCCATG GCCGAYATTTTGCTGACTCAGTC |
| Primer 9 | SEQ ID NO: 10 | CCTTTCTATGCGGCCCAGCCGGCCATG GCCGAYATTGTTCTCAWCCAGTC |
| Primer 10 | SEQ ID NO: 11 | CCTTTCTATGCGGCCCAGCCGGCCATG GCCGAYATTGWGCTSACCCAATC |
| Primer 11 | SEQ ID NO: 12 | CCTTTCTATGCGGCCCAGCCGGCCATG GCCGAYATTSTRATGACCCARTC |
| Primer 12 | SEQ ID NO: 13 | CCTTTCTATGCGGCCCAGCCGGCCATG GCCGAYRTTKTGATGACCCAVAC |
| Primer 13 | SEQ ID NO: 14 | CCTTTCTATGCGGCCCAGCCGGCCATG GCCGAYATYCAGATGACACAGAC |
| Primer 14 | SEQ ID NO: 15 | CCTTTCTATGCGGCCCAGCCGGCCATG GCCGAYATTGTGATGACACAACC |
| Primer 15 | SEQ ID NO: 16 | CCTTTCTATGCGGCCCAGCCGGCCATG GCCGAYATCCAGCTGACTCAGCC |
| Primer 16 | SEQ ID NO: 17 | CCTTTCTATGCGGCCCAGCCGGCCATG GCCGAYATTGTGATGACBCAGKC |
| Primer 17 | SEQ ID NO: 18 | CCTTTCTATGCGGCCCAGCCGGCCATG GCCGAYATTGTGATAACYCAGGA |
| Primer 18 | SEQ ID NO: 19 | CCTTTCTATGCGGCCCAGCCGGCCATG GCCGAYATTGTGATGACCCAGWT |
| Primer 19 | SEQ ID NO: 20 | CCTTTCTATGCGGCCCAGCCGGCCATG GCCGAYGTGSTGMTSACYCAGTC |
| Primer 20 | SEQ ID NO: 21 | CCTTTCTATGCGGCCCAGCCGGCCATG GCCGAYGCTGTTGTACTCAGGAATC |
| Primer 21 | SEQ ID NO: 22 | CCTTTCTATGCGGCCCAGCCGGCCATG GCCGAYATTGTDHTVWCHCAGTC |

TABLE 2

| Primer 22 | SEQ ID NO: 23 | AGCGGCGGCGGCGGCTCTGGTGGTGGTGGATCCG AKGTRMAGCTTCAGGAGYC |
|---|---|---|
| Primer 23 | SEQ ID NO: 24 | AGCGGCGGCGGCGGCTCTGGTGGTGGTGGATCCG AGGTNCAGCTBCAGCAGTC |
| Primer 24 | SEQ ID NO: 25 | AGCGGCGGCGGCGGCTCTGGTGGTGGTGGATCCC AGGTGCAGCTGAAGSASTC |
| Primer 25 | SEQ ID NO: 26 | AGCGGCGGCGGCGGCTCTGGTGGTGGTGGATCCC AGSTBCAGCTGCAGCAGTC |
| Primer 26 | SEQ ID NO: 27 | AGCGGCGGCGGCGGCTCTGGTGGTGGTGGATCCG AGGTYCAGCTYCAGCAGTC |
| Primer 27 | SEQ ID NO: 28 | AGCGGCGGCGGCGGCTCTGGTGGTGGTGGATCCG ARGTCCARCTGCAACARTC |
| Primer 28 | SEQ ID NO: 29 | AGCGGCGGCGGCGGCTCTGGTGGTGGTGGATCCC AGGTYCAGCTBCAGCARTC |
| Primer 29 | SEQ ID NO: 30 | AGCGGCGGCGGCGGCTCTGGTGGTGGTGGATCCC AGGTYCARCTKCAGCAGTC |
| Primer 30 | SEQ ID NO: 31 | AGCGGCGGCGGCGGCTCTGGTGGTGGTGGATCCC AGGTCCACGTGAAGCAGTC |
| Primer 31 | SEQ ID NO: 32 | AGCGGCGGCGGCGGCTCTGGTGGTGGTGGATCCG AGGTGAASSTGGTGGARTC |
| Primer 32 | SEQ ID NO: 33 | AGCGGCGGCGGCGGCTCTGGTGGTGGTGGATCCG AVGTGAWGYTGGTGGAGTC |
| Primer 33 | SEQ ID NO: 34 | AGCGGCGGCGGCGGCTCTGGTGGTGGTGGATCCG AGGTGAAGGTCATCGAGTC |
| Primer 34 | SEQ ID NO: 35 | AGCGGCGGCGGCGGCTCTGGTGGTGGTGGATCCS AGGTGCAGSKGGTGGAGTC |
| Primer 35 | SEQ ID NO: 36 | AGCGGCGGCGGCGGCTCTGGTGGTGGTGGATCCG AKGTGCAMCTGGTGGAGTC |
| Primer 36 | SEQ ID NO: 37 | AGCGGCGGCGGCGGCTCTGGTGGTGGTGGATCCG AAGTGCAVCTGGTGGAGTC |
| Primer 37 | SEQ ID NO: 38 | AGCGGCGGCGGCGGCTCTGGTGGTGGTGGATCCG AGGTGAAGCTGATGGARTC |
| Primer 38 | SEQ ID NO: 39 | AGCGGCGGCGGCGGCTCTGGTGGTGGTGGATCCG AGGTGCARCTTGTTGAGTC |
| Primer 39 | SEQ ID NO: 40 | AGCGGCGGCGGCGGCTCTGGTGGTGGTGGATCCG ARGTRAAGCTTCTCGAGTC |
| Primer 40 | SEQ ID NO: 41 | AGCGGCGGCGGCGGCTCTGGTGGTGGTGGATCCG AAGTGAARSTTGAGGAGTC |
| Primer 41 | SEQ ID NO: 42 | AGCGGCGGCGGCGGCTCTGGTGGTGGTGGATCCG AAGTGATGCTGGTGGAGTC |
| Primer 42 | SEQ ID NO: 43 | AGCGGCGGCGGCGGCTCTGGTGGTGGTGGATCCC AGGTTACTCTRAAAGWGTSTG |
| Primer 43 | SEQ ID NO: 44 | AGCGGCGGCGGCGGCTCTGGTGGTGGTGGATCCC AGGTCCAAYTVCAGCARCC |
| Primer 44 | SEQ ID NO: 45 | AGCGGCGGCGGCGGCTCTGGTGGTGGTGGATCCG ATGTGAACTTGGAAGTGTC |

TABLE 3

| Primer 45 | SEQ ID NO: 46 | ACCAGAGCCGCCGCCGCCGCTACCACCACCACCC CGTTTGATTTCCARCTTKG |
|---|---|---|
| Primer 46 | SEQ ID NO: 47 | ACCAGAGCCGCCGCCGCCGCTACCACCACCACCC CGTTTTATTTCCAGCTTGG |
| Primer 47 | SEQ ID NO: 48 | ACCAGAGCCGCCGCCGCCGCTACCACCACCACCC CGTTTSAGCTCCAGCTTGG |
| Primer 48 | SEQ ID NO: 49 | ACCAGAGCCGCCGCCGCCGCTACCACCACCACCC CGTTYWATTTCCAACTTWG |
| Primer 49 | SEQ ID NO: 50 | ACCAGAGCCGCCGCCGCCGCTACCACCACCACCC CCTAGGACAGTCAGTTTGG |

TABLE 4

| | | |
|---|---|---|
| Primer 50 | SEQ ID NO: 51 | CGGCACCGGCGCACCTGCGGCCGCYGAGGAAA CGGTGACCGTGGT |
| Primer 51 | SEQ ID NO: 52 | CGGCACCGGCGCACCTGCGGCCGCYGAGGAGA CTGTGAGAGTGGT |
| Primer 52 | SEQ ID NO: 53 | CGGCACCGGCGCACCTGCGGCCGCYGAGGAGA CGGTGACTGAGRT |
| Primer 53 | SEQ ID NO: 54 | CGGCACCGGCGCACCTGCGGCCGCYGAGGAAG ACTGTAGAGTGGT |
| Primer 54 | SEQ ID NO: 55 | CGGCACCGGCGCACCTGCGGCCGCYGCGGAGA CASTGACCAGAGT |
| Primer 55 | SEQ ID NO: 56 | CGGCACCGGCGCACCTGCGGCCGCYGCAGAGA CASTGACCAGAGT |

Step (a-1) Preparation of a Hybridoma (Derived from Mouse Spleen) Capable of Producing Monoclonal Antibodies which Specifically Bind to Troponin I Derived from Human Myocardium A peptide having an amino acid sequence (SEQ ID NO: 01, purchased from Sigma Aldrich Japan Co., Ltd., RPAPAPIR-RRSSNYRAYATEPHAKKKSKISAS-RKLQLKTLLLQIAK) contained in troponin I derived from human myocardium was connected to human serum albumin (purchased from Sigma Aldrich Japan Co. Ltd.) using a sulfo-SMCC cross linker (purchased from Servo Fischer Scientific Co., Ltd.).

More particularly, the sulfo-SMCC cross linker (0.5 mg) was dissolved in 100 microliters of a phosphate buffered saline so as to obtain a first aqueous solution. This first aqueous solution was left under a temperature of 50 degrees Celsius for ten minutes.

The human serum albumin (10 mg) was dissolved in one milliliter of a phosphate buffered saline to obtain a second aqueous solution.

The first aqueous solution was mixed with the second aqueous solution to obtain a mixture. The mixture was left at rest for 30 minutes. In this way, the sulfo-SMCC cross linker was connected to the human serum albumin.

The mixture was passed through a column (purchased from GE health care, trade name: PD10) to remove the unreacted sulfo-SMCC cross linker.

The above-mentioned peptide (SEQ ID NO: 01, 1.5 mg) was dissolved in dimethylsulfoxide (hereinafter, referred to as "DMSO") to obtain a DMSO solution. The DMSO solution (100 microliters) was added to the mixture (1 mL) having a concentration of 2 mg/ml. Afterwards, the mixture was left overnight to connect the sulfo-SMCC cross linker to the peptide (SEQ ID NO: 01).

In this way, human serum albumin modified with the peptide having the amino acid sequence (SEQ ID NO: 01) contained in the troponin I was obtained. Hereinafter, this human serum albumin is referred to as "troponin-modified HSA".

A complete Freud adjuvant (purchased from Wako Pure Chemical Industries Co., Ltd.) and the troponin-modified HSA were mixed to obtain a mixture. This mixture was injected to a BALB/c mouse. The BALB/c mouse is a kind of albino mouse.

Two weeks later, a mixture of phosphate buffered saline (hereinafter, referred to as "PBS") and troponin-modified HSA was injected into the BALB/c mouse. This was repeated once again. In this way, the BALB/c mouse was immunized by troponin-modified HSA for one month. In other words, by administering the mixture to the BALB/c mouse, antibodies against troponin-modified HSA were produced in the body of the BALB/c mouse.

The spleen of the immunized BALB/c mouse was taken out. In accordance with the cell fusion method disclosed in Non Patent Literature 4, hybridomas were obtained. Afterwards, the hybridomas were incubated in a culture fluid. The number of hybridomas (cells) after the incubation was approximately $5 \times 10^6$. The hybridomas obtained in this way were capable of producing the monoclonal antibody which specifically bound to troponin I derived from human myocardium.

Non Patent Literature 4

G. Kohler et al., Nature, 256, 495 (1975)

Step (a-2) Extraction of Total Mouse RNAs from the Hybridoma Cells

In order to destroy the cell membrane of the cultured hybridomas, one milliliter of TRIzol (Purchased from Invitrogen Co., Ltd.) was added to the culture fluid containing the hybridomas, and the culture fluid was stirred well.

Then, a chloroform liquid having a volume of 0.2 mL (degree of purity: 99.9%) was added to the culture fluid, and the culture fluid was stirred well again.

The culture fluid was subjected to a centrifugal separation at an acceleration of gravity of 117600 m/s² under a temperature of 4 degrees Celsius for 15 minutes. The supernatant (500 μL) was acquired. Isopropanol (500 μL) was added to the obtained supernatant and left at rest under room temperature for ten minutes.

The culture fluid was again subject to a centrifugal separation having a condition identical to the above-mentioned condition to obtain a precipitate. A seventy-five percent ethanol aqueous solution (1 mL) was added to the obtained precipitate so as to obtain an ethanol solution.

The ethanol solution was subjected to a centrifugal separation at an acceleration of gravity of 73500 m/s² for five minutes. The precipitate was dried. In this way, total mouse RNAs were obtained.

Step (b-1) Extraction of mRNA from the Total Mouse mRNAs

Using an Oligotex™-dT30 <Super> mRNA Purification kit (purchased from Takara bio Co., Ltd.), mRNA was extracted from the total mouse RNAs obtained in the step (a-2).

RNase-free water (100 μl) was injected into a microtube. This microtube was set at a block incubator (purchased from ASTEC CO. LTD.) and heated under a temperature of 70 degrees Celsius for one hour.

The total mouse RNAs were dissolved in the RNase-free water (100 μL).

A 2× binding buffered solution (100 μL) included in the kit and an oligotex (10 μL) included in the kit were mixed with the RNase-free water (100 μL). Subsequently, the mixture was left at rest under a temperature of 70 degrees Celsius for three minutes. Furthermore, the mixture was left at rest under room temperature for ten minutes.

The mixture was subjected to a centrifugal separation at an acceleration of gravity of 147000 m/s² for five minutes. The supernatant was removed, and the precipitate was suspended in Wash buffer (350 μL) included in the kit. The suspension liquid was supplied to a column included in the kit. The column was subjected to a centrifugal separation at an acceleration of gravity of 147000 m/s² for 30 seconds.

The Wash buffer (350 μL) was supplied to the column to wash the column. The column was subjected to a centrifugal separation at an acceleration of gravity of 147000 m/s² again for 30 seconds.

A microtube for sample collection was attached to the bottom of the column.

In order to extract mRNA contained in the column, RNase-free water (20 μL) contained in the microtube was supplied to the column. Subsequently, the column was subjected to a centrifugal separation at an acceleration of gravity of 147000 m/s² for three minutes. Again, RNase-free water (20 μL) was supplied to the column, and the column was subjected to a centrifugal separation at an acceleration of gravity of 147000 m/s² for three minutes.

Thus, the extract liquid containing the mRNA was obtained in the microtube.

(Step b-2) Reverse-Transcription from mRNA to cDNA

The mRNA contained in the obtained extract liquid was reverse-transcripted with a reverse-transcriptase (purchased from Takara bio Co., Ltd, trade name: Primersript) to obtain a solution containing cDNA.

Step (b-3-1) Amplification of the Gene Coding for the Light Chain Variable Region Using the cDNA The gene fragment (SEQ ID NO: 58, hereinafter, referred to as "VL gene fragment") coding for the light chain variable region of the above-mentioned monoclonal antibody was amplified by a PCR method using the cDNA contained in the solution, the forward primers 1-21 (SEQ ID NOS: 02-22), and the reverse primers 1-5 (SEQ ID NOS: 23-27). The polymerase used in this PCR method was purchased from Takara bio Co., Ltd under a trade name of TaKaRa Ex Taq Hot start Version.

The protocol of this PCR method is shown in Table 5.

TABLE 5

| One cycle | ninety six degrees Celsius for thirty seconds |
| | fifty two degrees Celsius for one minute |
| | sixty eight degrees Celsius for one minute |

The number of the cycles: 35.

Finally, the solution was left at 68 degrees Celsius for four minutes. In this way, a PCR solution was obtained. This PCR solution contained the amplified VL gene fragment (SEQ ID NO: 58).

For the confirmation and purification of the amplified VL gene fragment, the obtained PCR solution was subjected to an electrophoresis using a gel containing agarose having a concentration of 2% by weight.

Step (b-3-2) Amplification of the Gene Coding for the Heavy Chain Variable Region Using the cDNA The gene fragment (SEQ ID NO: 57, hereinafter, referred to as "VH gene fragment") coding for the heavy chain variable region of the above-mentioned monoclonal antibody was amplified by a PCR method using the cDNA contained in the solution, the forward primers 22-44 (SEQ ID NOS: 28-50), and the reverse primers 6-11 (SEQ ID NOS: 51-56). The polymerase used in this PCR method was purchased from Takara bio Co., Ltd under a trade name of TaKaRa Ex Taq Hot start Version.

The protocol of this PCR method was identical to that used for the VL gene fragment.

Finally, the solution was left at 68 degrees Celsius for four minutes. In this way, a PCR solution was obtained. This PCR solution contained the amplified VH gene fragment (SEQ ID NO: 57).

For the confirmation of the generation of the VH gene fragment and for the purification of the VH gene fragment, the obtained PCR solution was subjected to an electrophoresis using a gel containing agarose having a concentration of 2% by weight.

Step (b-4) Connection of the VL Gene Fragment and the VH Gene Fragment

The purified VH gene fragment (SEQ ID NO: 57) was connected to the purified VL gene fragment (SEQ ID NO: 58) using an overlap extension PCR method. In this way, the gene fragment (SEQ ID NO: 59, hereinafter, referred to as "scFv gene fragment") coding for the scFv antibody fragment of the above-mentioned monoclonal antibody was obtained. The obtained gene fragment (SEQ ID NO: 59) was modified with restriction enzyme sites Nco1 and Not1 at the 5'-end and 3'-end thereof, respectively.

Step (c-1) Introduction of the Gene to a Vector

The scFv gene fragment was ligated into a protein expression vector (purchased from Takara bio Co., Ltd, trade name: pET22b(+)). The detail of the ligation is described below.

First, the scFv gene fragment was treated with restriction enzymes Nco1 and Not1 (both of which were purchased from Takara bio Co., Ltd.). The scFv gene fragment was purified by an electrophoresis method to obtain an aqueous solution containing the scFv gene fragment.

The protein expression vector was also treated with restriction enzymes Nco1 and Not1 (both of which were purchased from Takara bio Co., Ltd.). The protein expression vector was also purified by an electrophoresis method to obtain an aqueous solution containing the protein expression vector.

These two aqueous solutions were mixed to obtain a mixture.

An enzyme (purchased from Toyobo Co., Ltd., trade name: Ligation High ver. 2) was added to the mixture, and the mixture was left under a temperature of 16 degrees Celsius for two hours. In this way, the scFv gene fragment was ligated into the protein expression vector. *Escherichia coli* cells (purchased from Takara bio Co., Ltd., trade name; DH5α competent cell) were transformed with the protein expression vector in which the scFv gene fragment was thus ligated.

Subsequently, the *Escherichia coli* cells were incubated for sixteen hours on an LB plate culture medium containing ampicillin having a concentration of 100 μg/mL. After the incubation, a single colony formed on the LB plate culture medium was picked up. The single colony was supplied to an LB liquid culture medium (5 mL) containing ampicillin having a concentration of 100 μg/mL, and the colony was incubated for 16 hours.

In order to remove an unnecessary gene sequence included in the protein expression vector pET22b(+), the protein expression vector pET22b(+) was extracted from this LB liquid culture medium using a kit (QIAGEN Co., Ltd. trade name: QIAprep spin miniprep kit). By a PCR method using the extracted protein expression vector pET22b(+), the primer 56 (SEQ ID NO: 67), and the primer 57 (SEQ ID NO: 68), the signal sequence (DNA sequence, SEQ ID NO: 60) of the protein expression vector pET22b(+) was removed. Thus, the expression vector coding for the wild type scFv antibody fragment was obtained.

Step (c-2) Introduction of the Mutations to the Vector

The expression vector obtained in the step (c-1) included the scFv gene fragment (SEQ ID NO: 59). Among the 729 bases constituting the scFv gene fragment (SEQ ID NO: 59) included in the expression vector, nine bases were substituted. In more detail, the $181^{St}$ thymine (T), the $182^{nd}$ cytosine (C), the $202^{nd}$ adenine (A), the $203^{rd}$ cytosine (C), the $208^{th}$ adenine (A), the $209^{th}$ guanine (G), the $214^{th}$ thymine (T), the $215^{th}$ cytosine (C), and the $216^{th}$ adenine (A) were substituted with guanine (G), adenine (A), guanine (G), adenine (A), guanine (G), adenine (A), guanine (G), adenine (A), and thymine (T), respectively.

Figure 2:
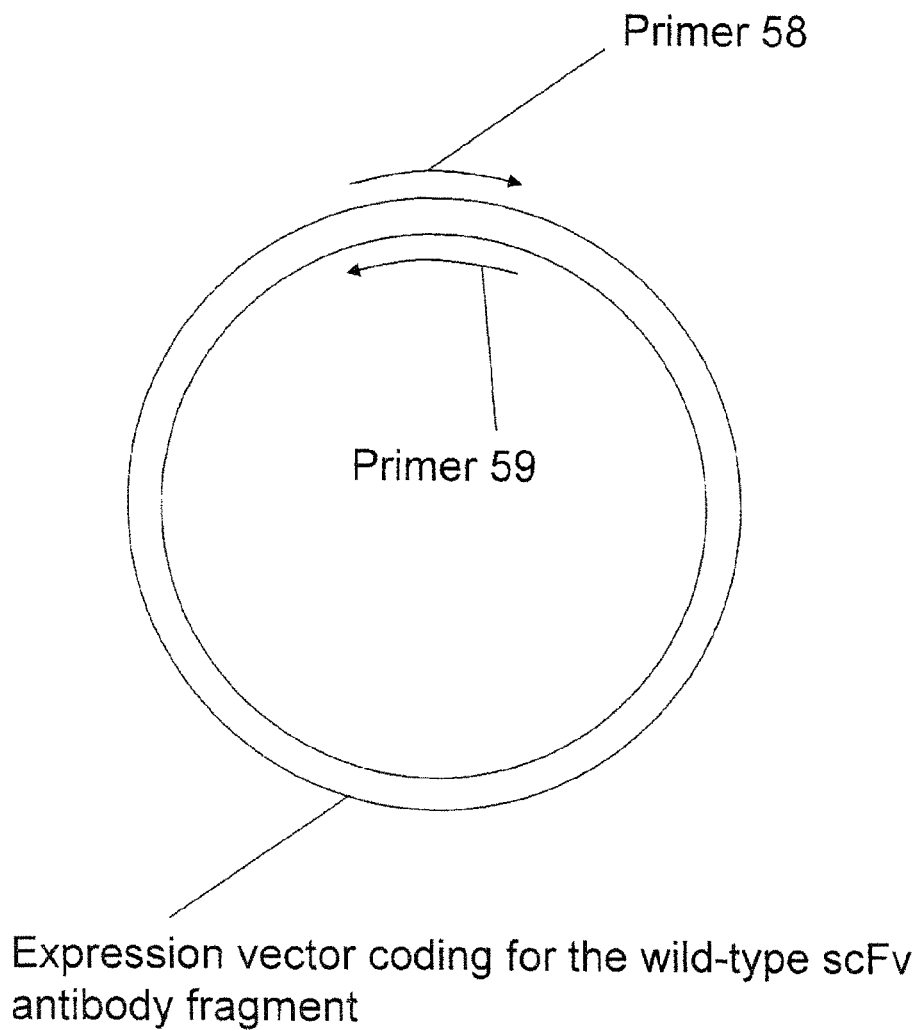
FIG. 2 shows a PCR method in the step (c-2).

More particularly, as shown in FIG. 2, a PCR method using the primer 58 (SEQ ID NO: 69), the primer 59 (SEQ ID NO: 70) and the expression vector obtained in the step (c-1) was performed. The primer 58 (SEQ ID NO: 69) was complementary to the gene sequence from $159^{th}$ base to $234^{th}$ base included in the scFv gene fragment (SEQ ID NO: 59) except for the nine bases to be substituted. The primer 59 (SEQ ID NO: 70) was complementary to the gene sequence from 159th base to 234th base included in the gene fragment complimentary to the scFv gene fragment (SEQ ID NO: 59) except for the nine bases to be substituted. The PCR method shown in FIG. 2 allowed the nine bases (TC, AC, AG, TCA) included in the expression vector coding for the wild type scFv antibody fragment to be substituted with the different nine bases (GA, GA, GA, GAT). Thus, the expression vector containing the gene sequence (SEQ ID NO: 71) encoding the mutant scFv was obtained.

Step (c-3) Acquisition of the Protein Using the Vector

*Escherichia coli* cells (purchased from Takara bio Co., Ltd, trade name: BL21(DE3)) were transformed with the vector obtained in the step (c-2). Subsequently, the *Escherichia coli* cells were incubated on an LB plate culture medium containing ampicillin having a concentration of 100 μg/mL under a temperature of 37 degrees Celsius for 16 hours.

After the incubation, a single colony formed on the LB plate culture medium was picked up. The single colony was supplied to an LB liquid culture medium containing ampicillin (500 mL) having a concentration of 100 μg/mL. Subsequently, the *Escherichia coli* cells contained in the single colony were propagated in such a manner that the absorbance of the LB liquid culture medium at a wavelength of 600 nanometers was adjusted to 0.5.

Furthermore, an aqueous solution of isopropyl beta-D-thiogalactopyranoside (0.5 mL) having a concentration of 1 M was added to the LB liquid culture medium. Afterwards, the *Escherichia coli* cells were incubated with shaking under a temperature of 37 degrees Celsius for five hours. In this way, a culture fluid was obtained.

The obtained culture fluid was subjected to a centrifugal separation at an acceleration of gravity of 49000 m/s$^2$ under a temperature of 4 degrees Celsius for five minutes. The precipitation containing the *Escherichia coli* cells was again suspended in a phosphate buffered saline (50 mL).

The suspension was subjected to an ultrasonic treatment to crush the *Escherichia coli* cells. The solution containing the crushed *Escherichia coli* cells was subjected to a centrifugal separation at an acceleration of gravity of 98000 m/s$^2$ under a temperature of 4 degrees Celsius for thirty minutes. In this way, the precipitation was obtained.

The precipitation was washed twice with a phosphate buffered saline containing a surface active agent (purchased from Wako Pure Chemical Industries Co., Ltd., trade name: Triton X-100) having a concentration of 4%. The precipitation was further washed with a phosphate buffered saline without containing a surface active agent.

An aqueous solution A (10 mL) containing chemical reagents shown in Table 6 was added to the precipitation.

TABLE 6

| Chemical reagents | Concentration |
| --- | --- |
| Guanidine hydrochloride | 6M |
| Sodium chloride | 0.1M |
| MES buffer solution | 50 mM |
| Ethylene diamine tetraacetic acid | 10 mM |

The aqueous solution A had a pH of 6.

Subsequently, the aqueous solution A was left under a temperature of 4 degrees Celsius for eighteen hours. In this way, the precipitation was dissolved.

The aqueous solution A was passed through a filter (purchased from Sartorius, trade name: Minisart) having a mesh size of 0.45 μm to remove the residue. In this way, the filtrate was obtained.

Two milliliters of an aqueous solution B was added dropwise to the filtrate (1 mL). The composition of the aqueous solution B (concentrations of chemical reagents contained in the aqueous solution B) is shown in Table 7.

TABLE 7

| Chemical reagents | Concentration |
| --- | --- |
| Tris-HCl | 0.1M |
| Ethylene diamine tetraacetic acid | 2 mM |
| Arginine hydrochloride | 1.0M |
| Cystamine | 3.73 mM |
| Cysteamine hydrochloride | 6.73 mM |

The aqueous solution B had a pH of 8.0. In this way, an aqueous solution having a volume of 3 mL was obtained.

The aqueous solution (3 mL) was added dropwise to an aqueous solution having a volume of one liter which contained the chemical reagents shown in Table 7. Afterwards, the obtained aqueous solution was stirred under a temperature of 4 degrees Celsius for 96 hours. In this way, the mutant scFv antibody fragment (SEQ ID NO: 61) was obtained.

Subsequently, the solution was concentrated using a filtration unit (purchased from Sartorius, trade name: VIVA-FLOW50) so that the solution had a volume of 10 milliliters. The mutant scFv antibody fragment contained in the solution was purified with a column (purchased from GE healthcare, trade name: HiLoad 26/60 Superdex pg).

The detail of the amino acid sequence (SEQ ID NO: 61) of the mutant scFv antibody fragment was described below.

```
Light chain variable region (SEQ ID NO: 63):
DVVLTQSPLTLSVTIGQPASISCKSSQSLLDSDGKTYLNWLLQRPGQSP

KRLIYLVSKLDDGVPDRFDGDGDGTDFTLKISRVEAEDLGVYYCWQGTH

FPLTFGAGTKLEIKR
```

The amino acid sequence modified at the N-terminal of the light chain variable region:

None

The amino acid sequence modified at the C-terminal of the light chain variable region:

None

```
Linker (SEQ ID NO: 64):
GGGGSGGGGSGGGGS

Heavy chain variable region (SEQ ID NO: 65):
QLQLQQSGAELVRSGASVKLSCTASGFNIKDYYMNWVKQRPEQGLEWIG

WIDPANGDTAYAPRFQVKATMTADKSSNTAYLQLSSLTSEDTAVYYCNA

DLPMDQWGQGTSVTVSS
```

The amino acid sequence modified at the N-terminal of the heavy chain variable region:

None

The amino acid sequence modified at the C-terminal of the heavy chain variable region:

```
                                      (SEQ ID NO: 66)
              AAALEHHHHHH
```

Step (d) Calculation of Association Rate Constant and Dissociation Rate Constant Using an intermolecular interaction analyzer Biacore T100 (purchased from GE health care company), the association rate constant and the dissociation rate constant of the mutant scFv antibody fragment were calculated in accordance with the manual attached to the intermolecular interaction analyzer Biacore T100.

Troponin I (purchased from Funakoshi) derived from human myocardium having approximately 500 RU (Resonance Unit) was fixed on a CM5 chip (purchased from GE health care company). This CM5 chip was set in the Biacore T100. Then, aqueous solutions (concentrations: 100 nM, 50 nM, 25 nM, 12.5 nM, and 6.25 nM; volume: 150 microliters) containing the mutant scFv antibody fragment was flowed through the Biacore T100. The association rate constant and the dissociation rate constant measured with the intermolecular interaction analyzer Biacore T100 are shown in Table 9.

Comparative Example 1

In Comparative Example 1, the experiment similar to Example 1 was conducted except that the step (c-2) was not conducted. In this way, the wild type scFv antibody fragment consisting of the amino acid sequence represented by SEQ ID NO: 62 was obtained. Similarly to Example 1, the association rate constant and the dissociation rate constant of the wild-type scFv antibody fragment were measured. The results are shown in Table 9.

The differences between the wild type scFv antibody fragment (SEQ ID NO: 62) and the mutant scFv antibody fragment (SEQ ID NO: 61) are shown in Table 8.

TABLE 8

|  | Wild type scFv antibody fragment (SEQ ID NO: 62) | Mutant scFv antibody fragment (SEQ ID NO: 61) |
|---|---|---|
| $61^{st}$ amino acid in the light chain variable region | S | D |
| $68^{th}$ amino acid in the light chain variable region | T | D |
| $70^{th}$ amino acid in the light chain variable region | S | D |
| $72^{nd}$ amino acid in the light chain variable region | S | D |
| Heavy chain variable region | (identical) | |

TABLE 9

|  | Comparative Example 1 | Example 1 |
|---|---|---|
| Association rate constant | $5.173 \times 10^{+4}$ | $1.324 \times 10^{+5}$ |
| Dissociation rate constant | $1.361 \times 10^{-4}$ | $1.015 \times 10^{-4}$ |

As is clear from Table 9, the mutant scFv antibody fragment according to Example 1 has a higher association rate constant than that of the wild-type scFv antibody fragment according to Comparative Example 1. This means that the mutant scFv antibody fragment bound specifically to troponin I derived from human myocardium more quickly than the wild-type scFv antibody fragment.

Industrial Applicability

The recombinant protein and the method according to the present disclosure can be used for a sensor for detecting acute myocardial infarction.

What is claimed is:

1. A recombinant protein which binds specifically to troponin I derived from human myocardium, the recombinant protein comprising:
   a light chain variable region consisting of the amino acid sequence represented by SEQ ID NO: 63; and
   a heavy chain variable region consisting of the amino acid sequence represented by SEQ ID NO: 65.

2. The recombinant protein according to claim 1, wherein the recombinant protein is an antibody.

3. The recombinant protein according to claim 1, wherein the recombinant protein is an antibody fragment.

4. The recombinant protein according to claim 3, wherein the antibody fragment is a Fab antibody fragment.

5. The recombinant protein according to claim 3, wherein the antibody fragment is a F(ab')$_2$ antibody fragment.

6. The recombinant protein according to claim 3, wherein the antibody fragment is an scFv antibody fragment.

7. A method for binding a recombinant protein specifically to troponin I derived from human myocardium, the method comprising:
   a step (a) of preparing the recombinant protein, wherein the recombinant protein comprises:
      a light chain variable region consisting of the amino acid sequence represented by SEQ ID NO: 63; and
      a heavy chain variable region consisting of the amino acid sequence represented by SEQ ID NO: 65; and
   a step (b) of bringing the recombinant protein into contact with the troponin I derived from human myocardium to bind the recombinant protein specifically to the troponin I derived from human myocardium.

8. The method according to claim 7, wherein the recombinant protein is an antibody.

9. The method according to claim 7, wherein the recombinant protein is an antibody fragment.

10. The method according to claim 9, wherein the antibody fragment is a Fab antibody fragment.

11. The method according to claim 9, wherein the antibody fragment is a F(ab')$_2$ antibody fragment.

12. The method according to claim 9, wherein the antibody fragment is an scFv antibody fragment.

* * * * *